United States Patent
Koslar

(10) Patent No.: US 6,453,200 B1
(45) Date of Patent: Sep. 17, 2002

(54) METHOD FOR WIRELESS COMMUNICATION TRANSFER WITH AN IMPLANTED MEDICAL DEVICE

(75) Inventor: Manfred Koslar, Berlin (DE)

(73) Assignee: Nanotron Gesellschaft fur Mikrotechnik mbH, Berlin (DE)

( * ) Notice: Subject to any disclaimer, the term of this patent is extended or adjusted under 35 U.S.C. 154(b) by 0 days.

(21) Appl. No.: 09/297,156

(22) PCT Filed: Nov. 3, 1997

(86) PCT No.: PCT/DE97/02590

§ 371 (c)(1),
(2), (4) Date: Apr. 26, 1999

(87) PCT Pub. No.: WO98/19591

PCT Pub. Date: May 14, 1998

(30) Foreign Application Priority Data

Nov. 1, 1996 (DE) .......................................... 196 46 746

(51) Int. Cl.$^7$ ................................................. A61N 1/08
(52) U.S. Cl. ........................................ 607/60; 600/509
(58) Field of Search ............................... 600/508–518; 607/60–61; 128/903

(56) References Cited

U.S. PATENT DOCUMENTS

| 3,969,725 A | 7/1976 | Couvillon et al. |
| 4,255,791 A | 3/1981 | Martin |
| 5,070,500 A | 12/1991 | Horinouchi et al. |
| 5,105,294 A | 4/1992 | Degura et al. |
| 5,113,278 A | 5/1992 | Degura et al. |
| 5,325,394 A | 6/1994 | Bruckert |
| 5,381,798 A | 1/1995 | Burrows |

FOREIGN PATENT DOCUMENTS

| DE | 36 18 416 | 3/1987 |
| DE | 39 28 571 | 3/1990 |
| DE | 32 16 666 | 11/1992 |
| DE | 196 01 866 | 8/1996 |
| EP | 223 554 | 5/1987 |
| WO | WO 95/20277 | 7/1995 |
| WO | WO 96/18913 | 6/1996 |

OTHER PUBLICATIONS

"Design of Cardiac Pacemakers" Webster, IEEE Press. TAB–IEEE Press Book Series.

Couch II, Leon W. *Digital and Analog Communication Systems*, Macmillan Publishing Co., NY, NY, 4th. ed. 1993.

Utlaut, W.F., "Spread–spectrum principles and possible application to spectrum utilization and allication", *telecommunication journal,* vol. 43, 1978, pp. 20–32.

Kowatsch et al., "Spread–Spectrum–übertragung analoger Signale mit Chirp–Modulation", Archiv Für Elektronik und Übertragungstechnik, vol. 36, Jul. 1982, pp. 299–304.

*Primary Examiner*—Mark Bockelman
(74) *Attorney, Agent, or Firm*—Altera Law Group LLC

(57) ABSTRACT

Disclosed herein is a method and apparatus for wireless communication with a medical device implanted in the human body. In the method disclosed herein an information input signal undergoes an angle modulation in a transmitter and reaches a receiver through a transmission channel. Angle modulated information carrying pulses with a frequency spectrum are generated. The pulses are time compressed in the receiver using a filter with frequency dependent transit time. The pulses are created with shortened duration and increased amplitude compared to emitted pulses. The pulses on the transmitter side are imprinted with at least part of information constituting a message using a further modulation or encoding procedure of telecommunications. At least part of the information constituting the message is additionally imprinted onto the angle modulation.

13 Claims, 9 Drawing Sheets

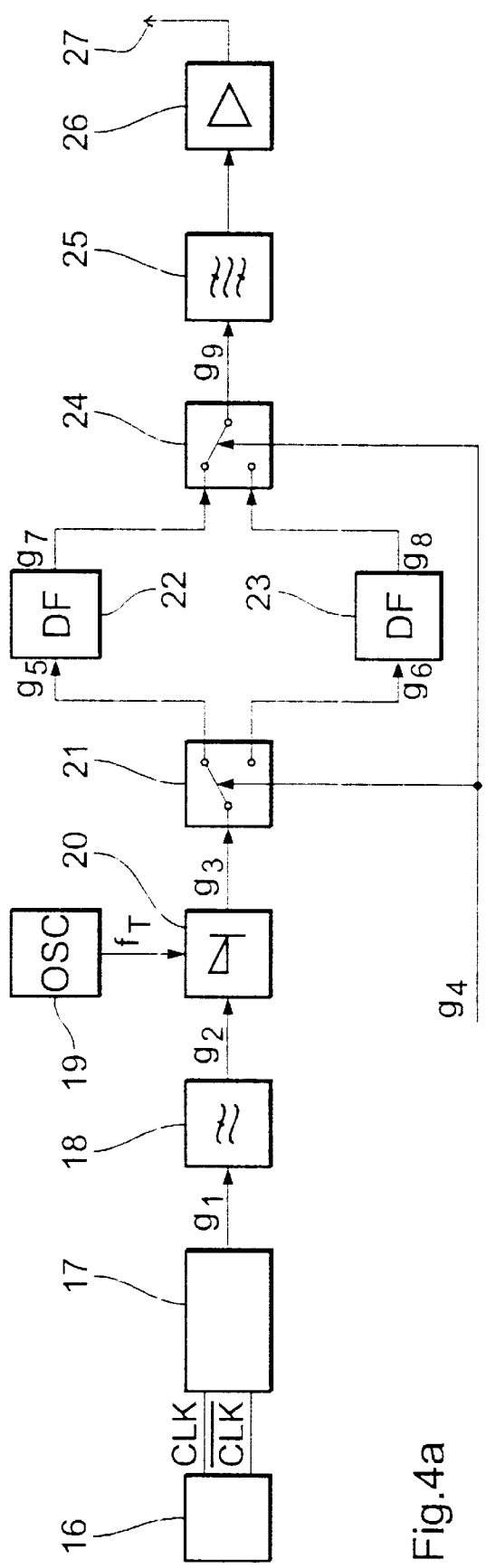
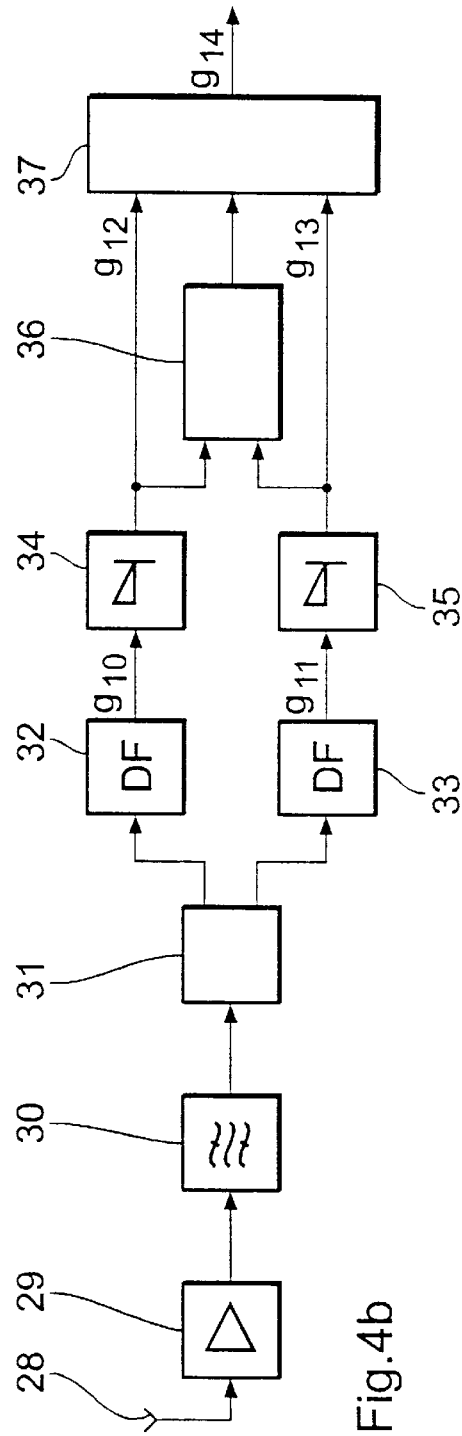
Fig.4a
Fig.4b

METHOD FOR WIRELESS COMMUNICATION TRANSFER WITH AN IMPLANTED MEDICAL DEVICE

BACKGROUND OF THE INVENTION

1. Field of the Invention

An early method for working with a high frequency carrier signal is disclosed in the German patent application DE 196 01 866.

Various methods and devices are known to transmit signals between a medical device, in particular an implanted one, and an external transmitter or receiver. For example, modern cardiac pacemakers can record an intracardial electrocardiogram (IECG) using the pacemaker electrodes and can transmit it, using a telemetry unit, to an extracorporeal control device.

2. Description of Related Art

In modern signal transfer methods that are known for implanted cardiac pacemakers, e.g. from the book by John G. Webster (Editor): "Design of Cardiac Pacemakers", section 12 "External Programming", IEEE Press Book Series, New York 1995, the digital signal that is to be transferred wirelessly is modulated onto the high frequency carrier signal in bit sequences by a modulator in the transmitter. It is then transmitted across a distance to the receiver, which contains a corresponding demodulator for recovery of the data signal. The carrier signal is in a comparatively low frequency range, since it has to penetrate the body and must not interfere with neighbouring medical devices.

All such methods have the disadvantage that the quality of the data signal that is recovered on the receiver side strongly deteriorates with the distance between transmitter and receiver, and with interference in the transmission path.

The transmitting power must not fall below a definite value, so that a desired range with a prescribed certain noise immunity can be achieved in an information transfer over a noisy transmission path.

This required high transmitting power, on one hand, has the disadvantage that the energy consumption during the transmitting operation is correspondingly high, which is of disadvantage for battery operated devices, such as the previously mentioned cardiac pacemakers, due to rapid battery exhaustion. On the other hand, one is concerned that the electromagnetic radiation emitted from the transmitter can lead to harm to the human body, which must in particular be considered for implanted medical devices due to the extremely low distance from the patient.

SUMMARY OF THE INVENTION

The objective of this invention is to create a method of the previously mentioned type and an arrangement for the implementation of that method, which allows a lowering of the transmitting power and an increase in range for medical implants—while at least maintaining the transmission quality.

The invention incorporates the technical principle, to subject the pulses, modulated with the information, using a known method of telecommunications, to an angle modulation in the transmitter. (Angle modulation is to be read as a generic term for phase and frequency modulation) These angle modulated pulses are time compressed in the receiver by introducing a time delay using suitable means, so that the duration of the pulses is shortened and they experience an amplitude enhancement. This pulse compression can be carried out using a dispersion filter. The information can be recovered from the pulses processed in this manner by a corresponding demodulation, whereby the demodulation can be carried out with an improved signal/noise ratio, due to the increase in amplitude. The actual information can be imprinted onto the pulse by a pulse modulation method, or by carrying out the pulse compression in a discernibly different manner for pulses sequential in time, so that the information is contained in this variation of the angle modulation.

Thus a signal is available after the demodulation, that otherwise could only be obtained by using higher transmitting power, if not using any other costly methods to improve reception, such as diversity reception or signal encoding, which occupies a larger frequency range or a longer transmission time due to redundant components, so that the available data channel would show a lower data throughput or could only be used by a lower number of users.

In this invention, the angle modulation of the pulses in the transmitter is carried out according to a modulation that, during the pulse duration, determines a change in frequency, in case of a frequency modulation, or a shift in phase, in case of a phase modulation. Phase and frequency modulation are both treated under the common generic term of angle modulation.

While the modulation of the pulses can be achieved using different pulse modulation methods, in the variable angle modulation a special angle modulation time characteristic is used, corresponding to a "modulation characteristic curve".

Hereby, the modulation characteristic curve—here referred to as modulation characteristic—determines the time behaviour of the frequency during the pulse duration. Preferably, the frequency of the transferred signal decreases linearly during the pulse duration, from a value above the carrier frequency to a value below the carrier frequency. The filter on the receiver side is matched to the employed modulation characteristic by a corresponding differential, frequency dependent delay time response, in such a manner so that the generated signal components of different phase position superpose to form a nearly coincident signal.

The imprinting of the information to be transmitted can occur either by varying or selecting the modulation characteristic, or by any other conventional modulation method that has no effect on the signal delay time, or only to a secondary degree. A preferred option is the modification of the amplitude of the transmitted signal dependent on the input signal—i.e. amplitude modulation, or all types of encoding in which the transmitted information is determined by the type, number, position, or sequence of the transferred pulses.

The invention offers in an advantageous manner the possibility to transmit signals to devices, in particular implanted ones, using higher frequencies than customary until now, without affecting the tissue on one hand, and without electromagnetic interference (EMI) to other devices used in the clinical environment on the other hand. Until now this was the main problem in the use of devices emitting electromagnetic waves in clinical surroundings. Until now these conditions ruled out, for example, the use of portable telephones etc. Additionally, this invention's method offers the advantage that a signal transfer can be made across larger distances (for example within a patient's room), so that programming devices etc. do not have to be attached directly to the patient's body. When appropriate codes are selected, it is also possible to communicate in parallel with several devices without mutual interference. Since the used signals can be transmitted with low amplitude, they do not rise above the surrounding noise level, or only negligibly. Thus the mutual interaction between them is low.

In a preferred embodiment of the invention the imprinting of the information of the input signal occurs by selecting or modifying a modulation characteristic dependent on the input signal. If the input signal has a high-level, then, for example, a modulation characteristic linearly falling with the signal is used, which leads to a frequency modulated pulse in which the frequency decreases during the pulse duration. For a low-level of the input signal a linearly rising modulation characteristic is used, which correspondingly leads to a pulse with frequency that increases during the pulse duration. The filter means on the receiver side are appropriately matched.

The invention is not limited to linear modulation characteristics, but can be implemented with modulation characteristics of any shape, whereby it is only necessary to assign distinct modulations to different levels of the input signals, so that a subsequent signal discrimination is possible in the receiver.

It is also possible to use more than two modulation characteristics for the input signal, so that every pulse transmits a larger information content. If, for example, four different modulation characteristics are available, then correspondingly four different pulses can be transmitted, which corresponds to a data content of 2 bits for each of the transmitted pulses. By increasing the number of distinct modulation characteristics the data transfer rate can be increased advantageously, whereby it must be noted that it becomes more difficult to distinguish between the frequency modulated pulses when a very large number of modulation characteristics are used, which increases the transfer's susceptibility to errors.

In the previously described embodiment of the invention the modulation of pulses occurs actively for both a high-level as well as for a low-level of the digital input signal. This means that during a low-level and a high-level of the input signal, frequency modulated pulses are generated, that are distinguished by the frequency change during the pulse duration. Thus hereby, the imprinting of the information contained in the input signal onto the transferred signal is achieved through selection or variation of the modulation characteristic depending on the input signal.

In another variation of the invention, the angle modulation of the pulses in the transmitter occurs independently of the input signal to be transmitted, according to a single default modulation characteristic, which determines the variation of frequency or phase during the duration of a pulse. The imprinting of the information contained in the input signal onto the transmitting signal can be effected in various ways, according to well known digital modulation methods. It is favourable to carry out a pulse position modulation (PPM), in which the position of the individual frequency modulated pulses is modified depending on the input signal.

In a preferred embodiment of the invention, the imprinting of the information contained in the input signal onto the transmitting signal is effected by pulse code modulation (PCM), in which the sequence of the pulses to be transferred is modified depending on the input signal. For a digital input signal the transfer of the input signal occurs actively only for one level, whereas no pulse is generated for the other level, so that the different pulses are only distinguished by their amplitude. For a high level of the input signal preferably a linearly rising frequency modulated pulse is generated, while for a low level a pause with the length of the pulse is inserted. This variation of the invention allows implementing a modulation of the pulses of the digital input signal with only one modulation characteristic.

In this present design for imprinting the information contained in the input signal onto the transmitting signal, the invention is not limited to the previously mentioned pulse position modulation or pulse code modulation, but can in principle be implemented with all known digital modulation methods.

The transmitter transfers the signal, frequency modulated by one of the previously described methods, across the transmission path to a receiver, where it is demodulated to recover the data signal.

Here, and in the following, the term transmission path should be taken generally, as comprising all wireless transmission paths in which the data transfer from the transmitter to the receiver occurs by means of electromagnetic waves.

To be able to distinguish the frequency modulated pulses, generated by the transmitter, from noise signals in the receiver, these pulses are compressed in the receiver, which leads to a corresponding increase in amplitude by increasing the signal/noise ratio.

A further advantage of this invention's method is a significantly lower interference potential compared to other transmitters and receivers, because a predetermined signal to noise ratio can be achieved with a lower transmitting power after the pulse compression in the receiver. In addition, the lower demands on the transmitting power lead to a lowered environmental impact by electromagnetic radiation.

To compress the pulses picked up on the receiver side, which are frequency modulated according to the modulation characteristic used by the transmitter, the received signal is filtered by a dispersion filter with a predetermined, frequency dependent, differential delay time response.

In the invention's variation that uses only a single modulation characteristic for generating a frequency modulated pulse on the transmitter side, described above, only a single dispersion filter is required on the receiver side, whereby the frequency dependent delay time response of this dispersion filter is matched to the modulation characteristic of the angle modulation carried out on the transmitter side in such a way, that the spectral signal components of the frequency modulated pulse generated on the transmitter side arrive essentially coincident at the output of the dispersion filter, which leads to a pulse compression and a corresponding increase in amplitude. If the angle modulation on the transmitter side is effected according to a linearly falling modulation characteristic, then the frequency of the pulse decreases during the pulse duration, which results in an arrival at the receiver of the high frequency signal components side before the low frequency signal components. The delay time response of the dispersion filter on the receiver side must compensate for this "lead" of the high frequency signal components, so that the spectral signal components of the frequency modulated pulse superpose to form a pulse with increased amplitude at the output of the dispersion filter.

The recovery of the information contained in the input signal is carried out by a detector connected after the dispersion filter, which is matched to the modulation method, that is used on the transmitter side for imprinting the information contained in the input signal.

If, depending on the amplitude of the input signal, one of several modulation characteristics is selected on the transmitter side, preferably a linearly falling modulation characteristic for a high-level, and a linearly rising modulation characteristic for a low-level of the input signal, then fundamentally two options exist for the interpretation in the receiver.

One option is to provide only one dispersion filter on the receiver side, the delay time response of which is matched to the modulation characteristic used on the transmitter side, in a manner so that the spectral signal components of the pulse, frequency modulated according to this modulation characteristic, arrive essentially coincident at the output of the dispersion filter, which leads to a pulse compression and increase in amplitude. If the frequency modulation on the transmitter side occurs according to one of the other modulation characteristics that are not optimally matched to the delay time response of the dispersion filter on the receiver side, then the spectral signal components of the frequency modulated pulse arrive at the output of the dispersion filter distributed over time, and thus, due to the lower pulse compression or expansion, also with a smaller amplitude. In this embodiment, the amplitude of the pulse that arrives at the output of the dispersion filter depends on the modulation characteristic used at the transmitter side, and thus on the amplitude of the input signal employed in the selection of the modulation characteristic. A detector that can be executed, for example, as an amplitude demodulator, is connected after the dispersion filter, to recover the digital input signal from the output signal of the dispersion filter.

In the other option the frequency modulated pulse is fed to several dispersion filters on the receiver side. The differential delay time response of the dispersion filters arranged on the receiver side and the modulation characteristics used on the transmitter side are hereby matched in pairs in such a way, that the spectral signal components of the frequency modulated pulse arrive essentially coincident at the output of exactly one of the dispersion filters, thus leading to an increase in amplitude, while the output signals of the other dispersion filters are not increased due to the differing characteristics. Thus the input signal can be discriminated according to which dispersion filter shows an increase in amplitude.

Advantageously, surface acoustic wave filters (English: SAW- Filter: Surface Acoustic Waves) are used as dispersion filters. Hereby a dispersion filter shows a frequency dependent, differential delay time response that is matched to the angle modulation carried out on the transmitter side, in such a way that the different spectral components of the transmitted signal arrive nearly coincident at the output of the dispersion filter in the receiver, due to their different transit times through the dispersion filter, so that the output amplitude is strongly increased by optimum superposition of the spectral components.

The generation of the frequency modulated signal in the transmitter can be achieved in various ways, some of which are briefly described in the following.

In a preferred embodiment of the invention, at first an approximate (quasi-) Dirac pulse is generated and fed to a low-pass filter, the filter characteristic of which shows a peak just before the critical frequency, and thus transforms the delta impulse to a Sinc-pulse, the shape of which is described by the Sinc-function $\mathrm{Sinc}(x)=\sin(x)/x$. The Sinc-shaped output signal of the low-pass filter subsequently is fed to an amplitude modulator that imprints a Sinc-shaped envelope onto the carrier oscillation. When the signal generated in this manner is fed to a dispersive filter, a frequency modulated pulse appears at its output. Thus in this variation of the invention, on the transmitter side the dispersion filter at first expands the relatively sharp Sinc-impulse into a frequency modulated pulse, that is wider, compared to the Sinc-pulse, and possesses a correspondingly lower amplitude. On the receiver side, a dispersion filter effects a compression of the pulse with a corresponding increase in amplitude. Since one dispersion filter each is used for the expansion of the pulses on the transmitter side, and the compression on the receiver side, this variation is advantageously suited for a transceiver operation with alternating transmitting and receiving operation. For this, transmitter and receiver can each contain corresponding identical component modules, with one dispersion filter each, that are used for the generation of the frequency modulated pulse in transmitting operation, and for the compression of the received frequency modulated pulses in receiving mode.

In another variation of the invention, the generation of the frequency modulated pulses is effected using a PLL (PLL: Phase Locked Loop) and a voltage controlled oscillator (VCO: Voltage Controlled Oscillator). The individual pulses of the input signal that is present in digital form are hereby at first converted to saw-tooth shaped pulses in an integrator, whereby the direction of the rise of the individual pulses depends on the amplitude of the input signal. The signal generated in this manner is then used for controlling the VCO, so that the frequency of the output pulse linearly increases or decreases during the pulse duration, depending on the level of the input signal.

In a further variation of the invention, the generation of the frequency modulated pulse in the transmitter is effected by a digital signal-processing unit, which advantageously allows the implementation of any desired modulation characteristics.

In a message transfer system according to this invention, it is necessary to match the frequency dependent delay time response of the dispersion. filter used on the receiver side to the modulation characteristic of the frequency modulation carried out on the transmitter side, so that a pulse compression in the receiver can be achieved.

In a variation of the invention, matched transmitter-receiver pairs are produced for this purpose, so that no further tuning work is necessary when the system is brought into service. The previously mentioned dispersion filters preferably are executed as surface acoustic wave filters (SAW-Filter: Surface Acoustic Waves), since such filters can be produced with high accuracy and stability. In addition, such surface acoustic wave filters offer the advantage that amplitude response and phase response can be dimensioned independently of each other, which offers the possibility of implementing the narrow-band band-pass filter that is required in each receiver and the dispersion filter in one component. Such filters are known for other application areas, for example from the European patent application EP 0 0223 554 A2.

In another variation of the invention, the receiver is matched to the transmitter by varying the delay time response of the dispersion filter used on the receiver side.

Thus in one advantageous variation of the invention, the transmitter, during a matching process, emits a reference signal that preferably corresponds to a sequence of high-levels of the input signal, whereby the modulation characteristic of the frequency modulation carried out on the transmitter side, or the frequency dependent delay time response of the dispersion filter on the receiver side, are varied, until an optimum pulse compression and increase in amplitude is achieved on the receiver side. This variation is especially advantageous when using a digital signal processor for filtering and processing in the receiver, since such a signal processor in a simple manner allows a modification of the frequency dependent delay time response and a corresponding optimization, whereby the optimization process can be executed automatically using computer control.

In a further advantageous embodiment of this variation, the data transfer occurs block by block, whereby the matching process described above is carried out again for each block, to be able to dynamically compensate for fluctuations of the dispersion characteristics of the transmission path.

Other advantageous, further developments of the invention are illustrated in more detail in the following figures together with the description of the invention's preferred embodiment. The figures show:

BRIEF DESCRIPTION OF THE DRAWINGS

FIGS. 4a, 4b show in a block diagram the transmitter and receiver of such a message transfer system, with active transmission of high and low levels.

DETAILED DESCRIPTION OF THE INVENTION

Figure 1A:
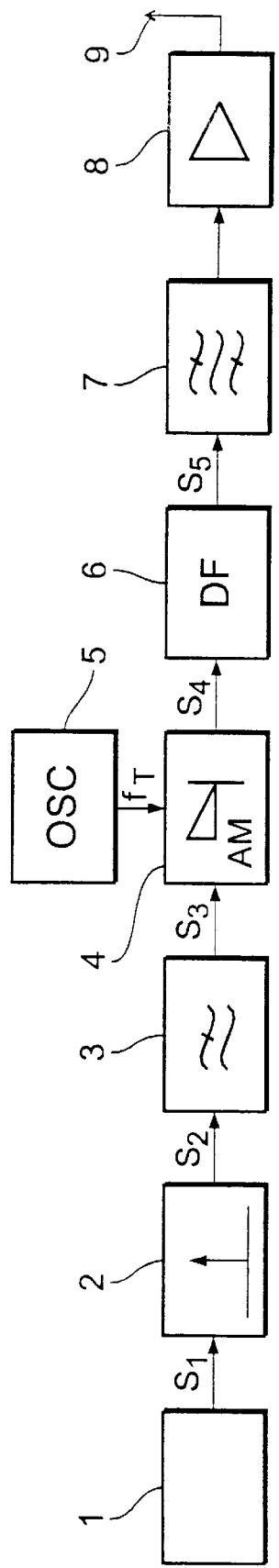
FIGS. 1a, 1b show, as the invention's preferred embodiment, a transmitter and receiver for data transfer from an implanted medical device to an extracorporeal control unit.
Figure 1B:
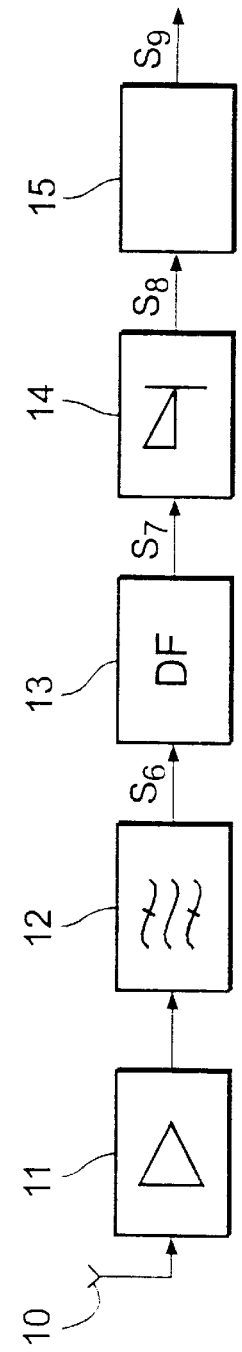

The transmitter illustrated in FIG. 1a is used for data transfer from an implanted medical device to an extracorporeal control unit. For example, it is possible to record an intracardial electrocardiogram (IECG) using the electrodes of a cardiac pacemaker, and to transmit it to a extracorporeal control unit, which displays the IECG on a monitor and subjects it to further signal processing for diagnostic purposes. The transmitter shown in FIG. 1a, together with the receiver shown in FIG. 1b, is well suited for this application, because the transmission can occur with relatively low transmitting power for predetermined requirements on range and noise immunity, which on one hand increases the battery life, and on the other hand reduces the environmental impact by electromagnetic radiation, also known as Electro-smog. In addition, the transmitter has a reduced interference potential compared to other communications systems due to the relatively low transmitting power.

Figure 2A:
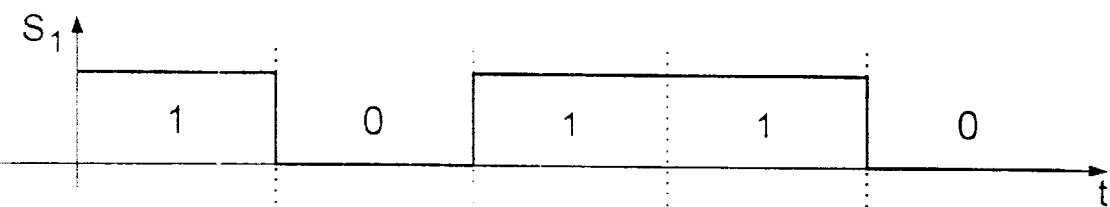
FIGS. 2a to 2e show the transmitter's digital input signal, as well as several intermediary stages of the signal processing in the transmitter up to the transmission signal.
Figure 2B:
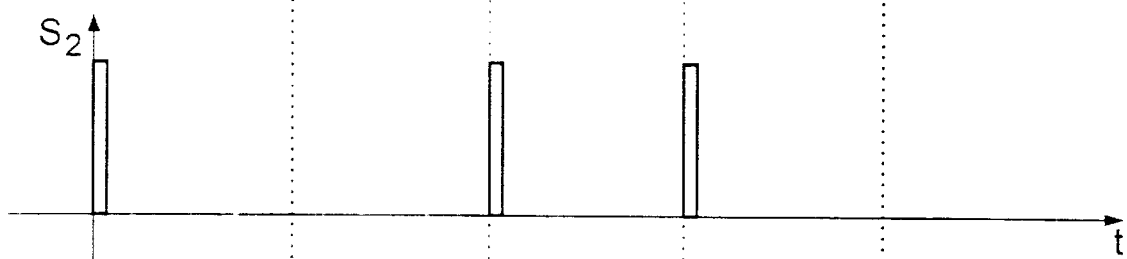

A digital input signal $s_1$, the time behaviour of which is shown in detail in FIG. 2a, generated for example by digitizing the IECG signal, in the transmitter is fed to a pulse shaper 2, which transforms the comparatively wide square pulses of the input signal $s_1$ into short needle impulses, that emulate (quasi-) Dirac pulses. It can be seen from the illustration of the needle pulse sequence $S_2$ in FIG. 2b that the generation of the individual needle pulses is triggered by the rising edges of the square pulses of input signal $s_1$.

Figure 2C:
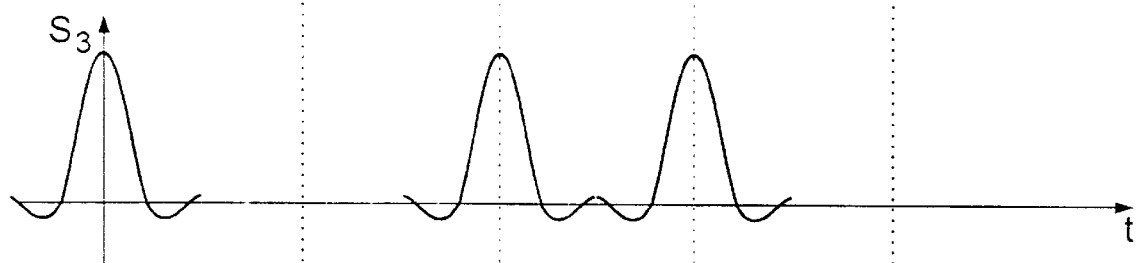

A needle pulse sequence $s_2$ generated in this manner is subsequently fed to a low-pass filter 3, the filter characteristic of which possesses a peak shortly before the critical frequency, so that the individual needle pulses—as seen in FIG. 2c—are transformed to Sinc-pulses, the shape of which corresponds to the well known Sinc-function Sinc(x)=sin (x)/x.

Figure 2D:
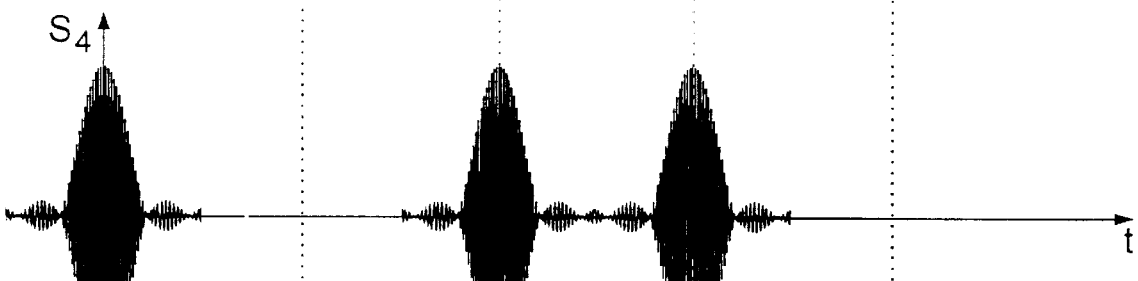

Subsequently, the Sinc-pulse sequence $s_3$ is fed to an amplitude modulator 4 (or amplitude multiplier) which modulates this signal onto a carrier oscillation of frequency $f_T$, generated by oscillator 5, so that carrier frequency pulses with a Sinc-shaped envelope are generated at the output of the amplitude modulator, as shown in FIG. 2d. (For representative reasons the pulses are shown widened in this diagram, thus in a scale representation they are narrower.)

Figure 2E:
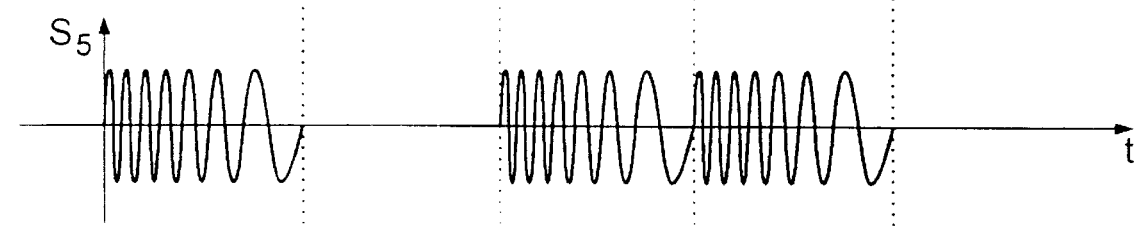

A dispersion filter 6 is connected after the amplitude modulator 4, which filters the modulated carrier frequency signal $S_4$ according to its frequency dependent, differential delay time characteristics. At the output of the dispersion filter 6 arrive—as can be seen in FIG. 2e—linearly frequency modulated pulses with constant amplitude, the frequency of which decreases during the pulse duration from a value $f_T+\Delta f/2$ above the carrier frequency $f_T$ to a value $f_T-\Delta f/2$ below the carrier frequency.

Thus in the transmitter shown here, the transmission of the input signal $s_1$ is made unipolar, i.e. a transmission pulse is only generated for a high level of the input signal $s_1$, while a low level can be recognized from a pause in the transmission signal $s_5$. For this reason transmitter and receiver can be constructed reasonably simply, each only containing one dispersion filter 6, 13.

The pulse sequence $s_5$ generated in this manner is subsequently fed to a band-pass filter 7, the centre frequency of which is equal to the carrier frequency $f_T$ of the frequency modulated pulses, so that signals outside the transmission band are filtered out.

Finally, the band-pass limited signal is supplied to antenna 9 by a transmitter amplifier 8 and emitted.

The receiver shown in FIG. 1b allows the reception of the linearly frequency modulated signal, emitted by the transmitter described above, as well as the demodulation and recovery of the digital input signal $S_3$ or $s_1$.

Figure 3A:
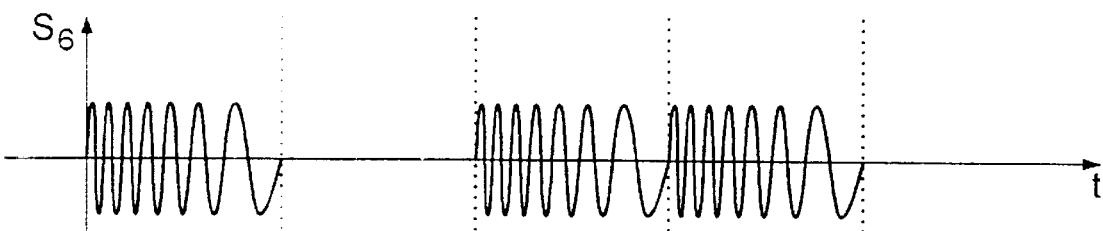
FIGS. 3a to 3d show the received signal as well as several intermediary stages in the signal processing in the receiver up to the demodulated signal.

For this, the signal received by the receiver's antenna 10—for example in diversity operation—is fed to a pre-amplifier 11 and subsequently a band-pass filter 12, the centre frequency of which is equal to the carrier frequency $f_T$ of the band-pass limited transmission signal, so that noise signals from other frequency ranges can be filtered out of the receiver signal. (Instead of a conventional band-pass filter a surface acoustic wave filter can be used here.) The time behaviour of the signal s6 prepared in this manner is shown in detail in FIG. 3a, whereby for simplification a noise free transmission path is assumed.

The received signal s6 consists of a series of linearly frequency modulated pulses, whereby the frequency decreases during the pulse duration, according to the modulation characteristic used on the transmitter side, from a value fT+Δf/2 above the carrier frequency fT to a value fT-Δf/2 below the carrier frequency.

Subsequently the signal s6 is fed to a dispersion filter 13, which time compresses the individual pulses of the input signal s6, which leads to a corresponding increase in amplitude, and thus an improved signal/noise ratio.

Figure 3B:
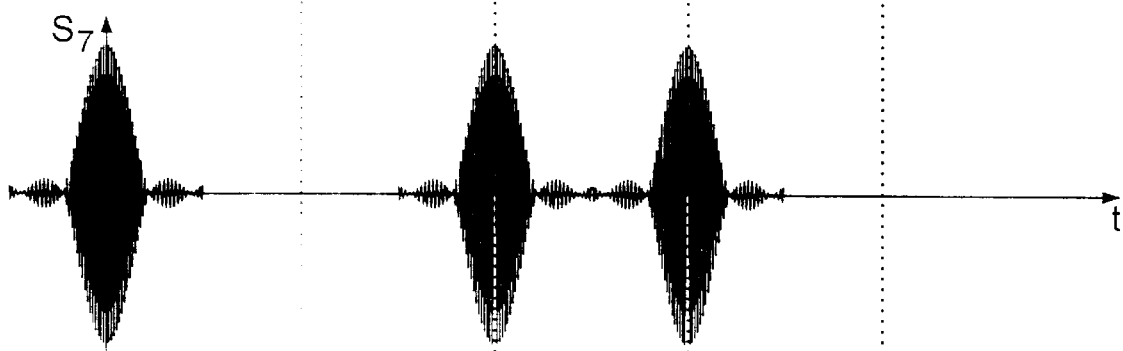

Hereby the pulse compression utilizes the fact that the signal components of higher frequency arrive at the output of the dispersion filter 13 before the lower frequency signal components, due to the linear frequency modulation carried out on the transmitter side. The dispersion filter 13 compensates for the "lead" of the higher frequency signal components by delaying these more than the lower frequency signal components. Hereby the frequency dependent, differential delay time response of dispersion filter 13 is matched to the modulation characteristic of the frequency modulation carried out on the transmitter side, in such a manner, that the spectral signal components of the received signal arrive essentially coincident at the output of dispersion filter 13. As seen in FIG. 3b, the spectral components superpose to form a signal s7 with Sinc-shaped envelope for each pulse, whereby the amplitude of the individual pulses is significantly increased compared to the received linear frequency modulated signal s6. (It should be noted at this point that for improved clarity a distortion was introduced in the schematic signal representations shown in the figures. In reality the frequency-modulated pulses are closer together and the compressed signals are much narrower.)

Figure 3C:
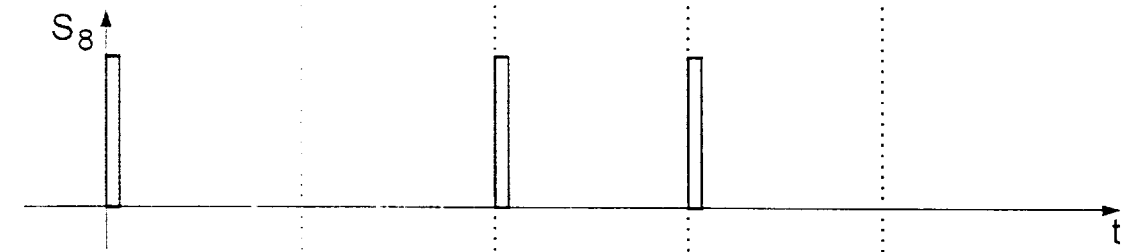

Subsequently the output signal of the dispersion filter 13 is fed to a demodulator 14, which separates signal s7 from the high frequency carrier oscillation and—as seen in FIG. 3c—generates a discrete output signal s8 with needle shaped pulses.

Figure 3D:
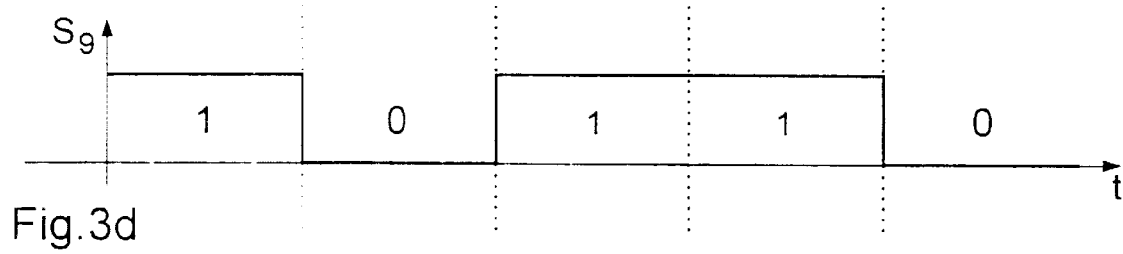

Subsequently, the original digital signal s9, the time behaviour of which is shown in detail in FIG. 3d, is recovered from the needle shaped pulses using a pulse shaper 15.

FIGS. 4a and 4b show a further message transfer system according to this invention, which differs from the simpler embodiment example, described above and illustrated in FIGS. 1a and 1b, most importantly by the fact that both the high level as well as the low level of the digital information signal are transmitted actively, which contributes to a higher noise immunity. This transmission system too is especially suited for data transfer from an implanted medical device to an extracorporeal control unit, due to the low demand on transmission power.

Figure 5A:
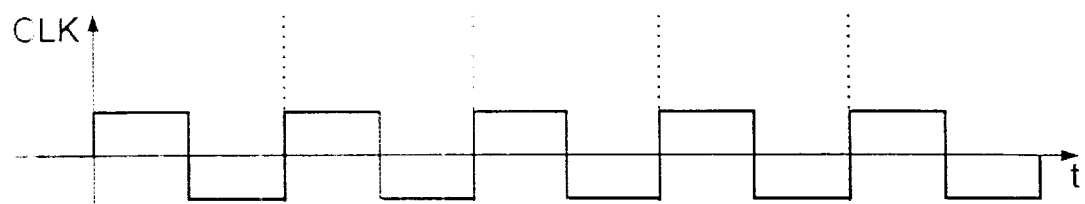
FIGS. 5a to 5k show the transmitter's digital input signal in FIG. 4a, as well as several intermediary stages of the signal processing in the transmitter.
Figure 5B:
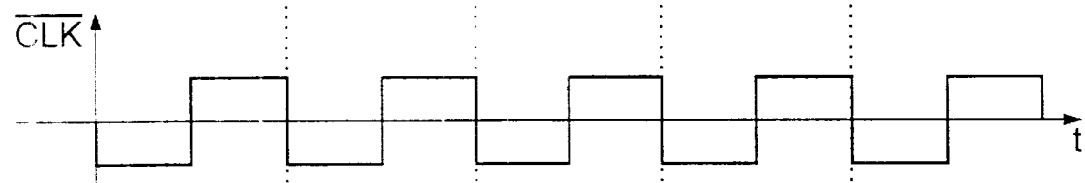
Figure 5C:
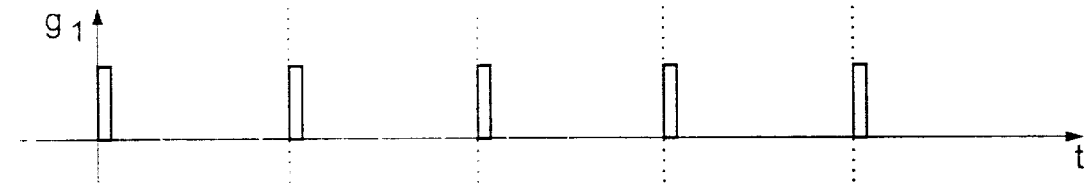
Figure 5D:
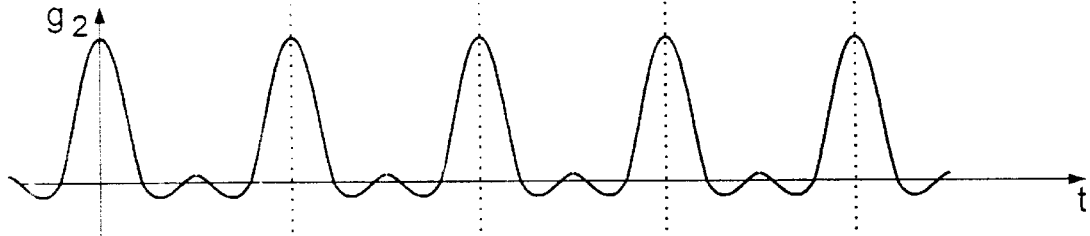
Figure 5E:
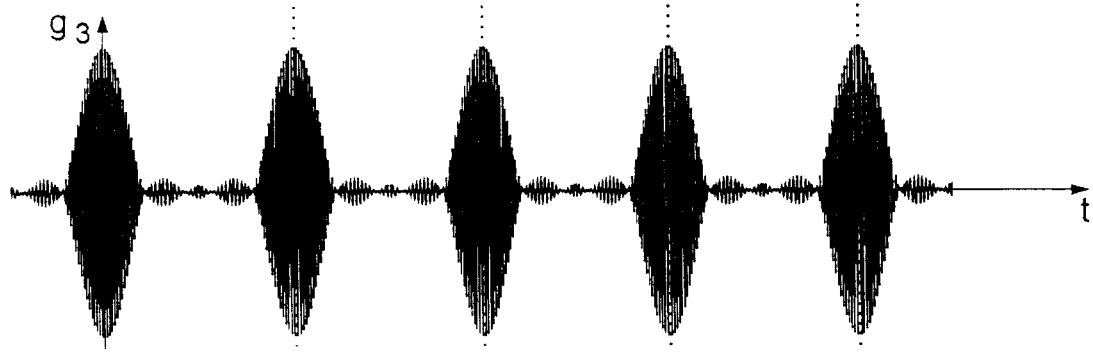
Figure 5F:
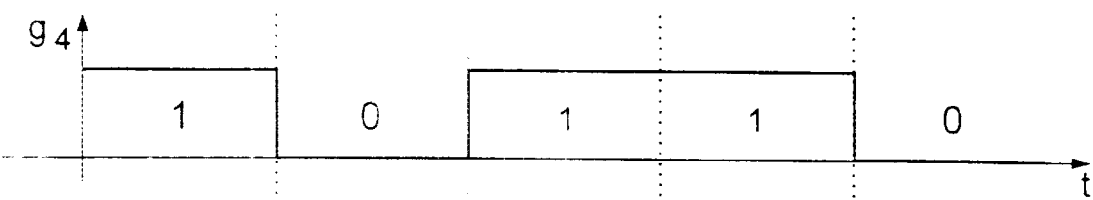
Figure 5G:
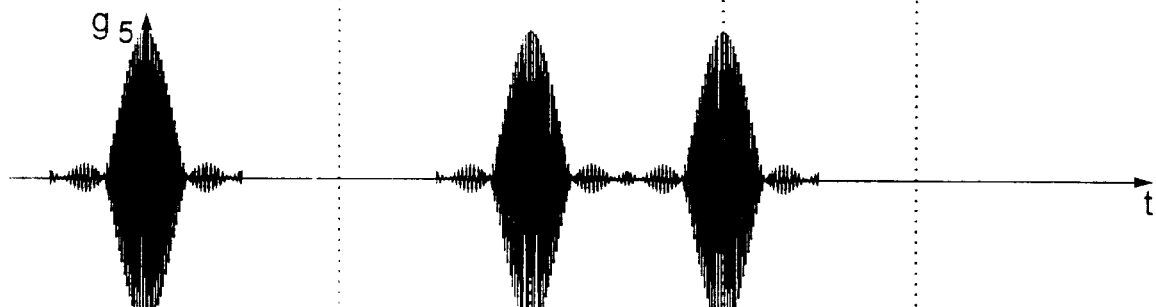
Figure 5H:
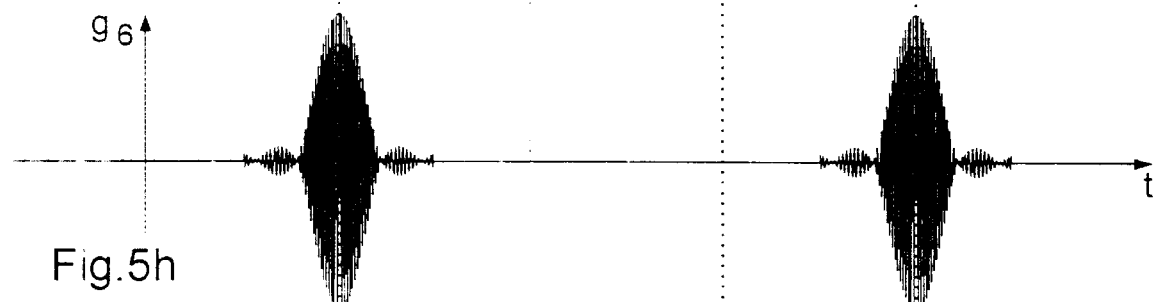
Figure 5I:
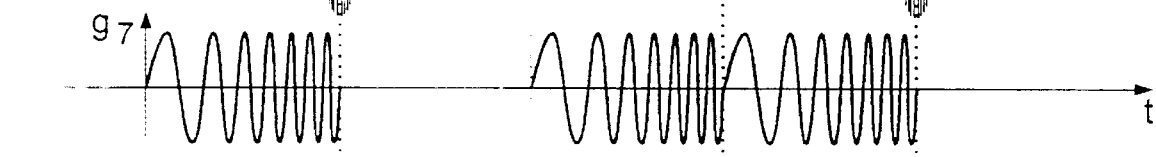
Figure 5J:
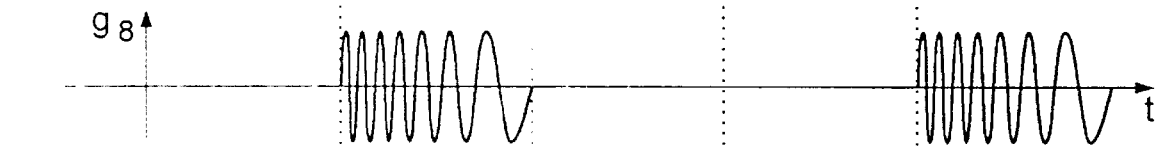

The transmitter shown in FIG. 4a contains a pulse shaper 17, which is triggered by a timing generator 16, using timing pulses opposite in phase, shown in FIGS. 5a, 5b. At its output the pulse shaper emits—as shown in FIG. 5c—a sequence g1 of needle shaped pulses that form a (quasi-) Dirac delta sequence. The pulse sequence g1 generated in this manner is subsequently fed to a low-pass filter 18, the filter characteristic of which possesses a peak just before the critical frequency, and that transforms the needle shaped pulses to Sinc-shaped pulses, which are shown in detail in FIG. 5d. Subsequently, this pulse sequence g2 is modulated onto a carrier oscillation with carrier frequency fT, generated by the oscillator 19, using an amplitude modulator 20. Thus, at the output of amplitude modulator 20 (or amplitude multiplier) arrives a sequence g3 of equidistant carrier frequency pulses with Sinc-shaped envelopes. It is important in this context, that the pulse sequence g3 arriving at the output of the amplitude modulator 20 is independent of the digital input signal g4, and thus does not contain any information.

Subsequently, the imprinting of the information of input signal g4 is effected by means of an analogue switch 21, which is controlled by input signal g4, and, depending on the amplitude of the input signal g4, directs the pulse sequence g3, generated by amplitude modulator 20, either to a dispersion filter 22 with a frequency dependent linearly decreasing delay time, or to a dispersion filter 23 with a frequency dependent linearly rising delay time. At their outputs, the dispersion filters 22, 23 are connected to a further analogue switch 24 or a mixer stage, which, depending on the amplitude of input signal g4, selects the output signal g7, g8 of one of the two dispersion filters 22, 23 and passes it on.

Figure 5K:
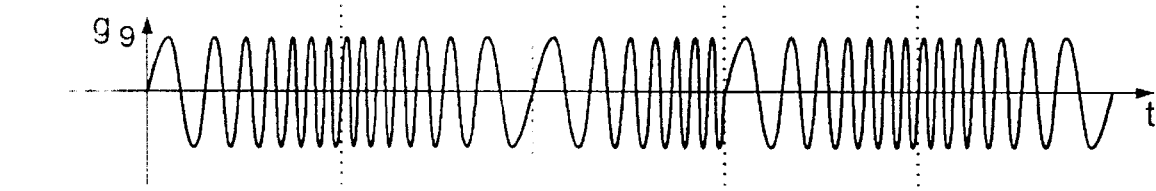

Thus at the output of the analogue switch 24 arrives—as shown in FIG. 5k—a sequence g9 of carrier frequency pulses, linearly frequency modulated pulse by pulse, whereby for a high level of the input signal g4 the individual pulses show a linearly increasing frequency during the pulse duration, whereas for a low level of input signal g4 the frequency during the pulse decreases linearly.

The signal arriving at the output of analogue switch 24 is subsequently filtered by band-pass filter 25 to suppress interference signals located outside of the transmission band. The signal obtained in this manner is then amplified by a transmitter amplifier 26 and is emitted by the transmitter antenna 27.

FIG. 4b shows the associated receiver that receives the signal, emitted by the transmitter shown in FIG. 4a, using an antenna 28. The receiver amplifies the signal in a preamplifier 29, and in a band-pass filter 30 removes any interference signals, the frequency of which lies outside the transmission band.

Subsequently, the received signal is carried to two dispersion filters 32, 33 by a switching element 31. Hereby the frequency dependent delay time response of the two dispersion filters 32, 33 on the receiver side is matched in pairs to the frequency dependent delay time response of the two dispersion filters 22, 23 on the transmitter side, in such a way that the spectral signal components of the received signal add to a pulse with increased amplitude at the output of one of the two dispersion filters, 32 or 33, while at the output of the other dispersion filter, 33 or 32, only an attenuated pulse arrives due to the mismatching.

Figure 6A:
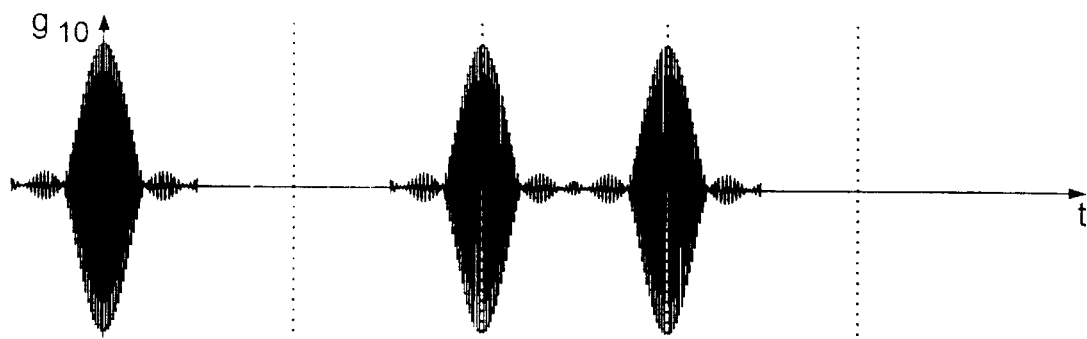
FIGS. 6a to 6e show the signal picked up on the receiver side, as well as several intermediary stages of the signal processing in the receiver.
Figure 6B:
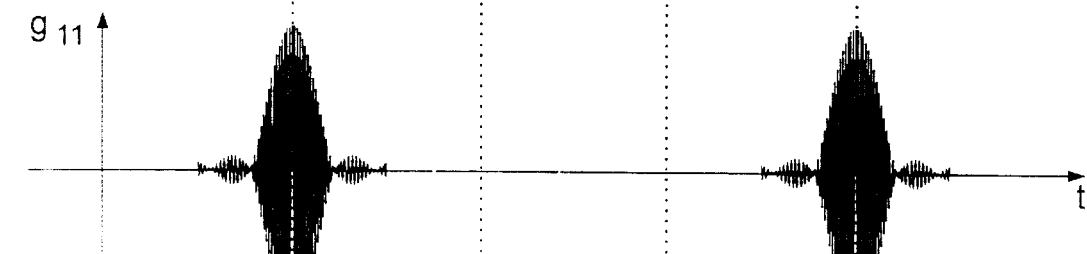

As seen in FIGS. 6a and 6b, the output signals g10 or g11 of dispersion filters 32, 33 consist of a sequence of carrier frequency pulses with Sinc-shaped envelopes.

Figure 6C:
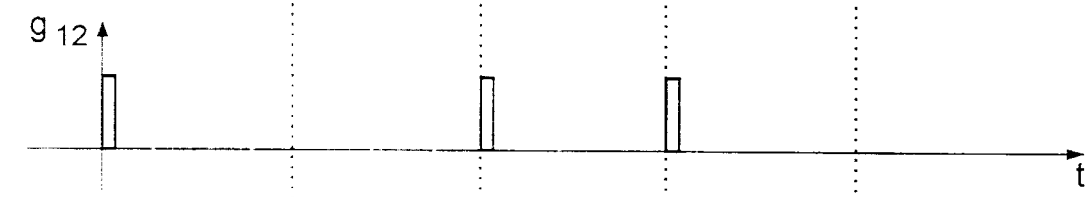
Figure 6D:
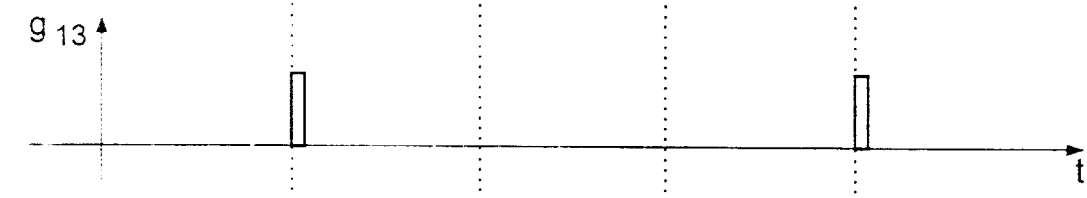

The signals g10 or g11, appearing at the output of the two dispersion filters 32, 33, are subsequently fed to a demodulator 34, 35, which separates the signals g10 or g11 from the carrier oscillation and generates needle shaped pulses, as seen in FIG. 6c or 6d.

While each of the needle impulses at the output of demodulator 34 corresponds to one high level of the input signal g4, the needle impulses arriving at the output of the other demodulator 35 indicate low levels of input signal g4.

Figure 6E:
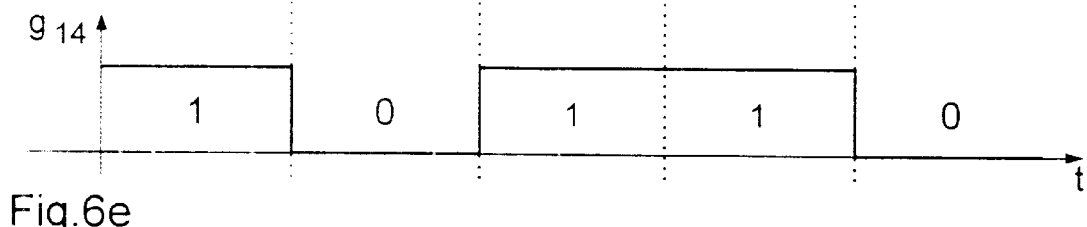

To recover the original input signal g4 from the two signals g12, g13, the two signals g12, g13 are fed to a timing generator 36 for triggering, which generates a timing signal that reproduces the timing signal, together with the output signals g12, g13 of the two demodulators 34, 35 is fed to the decode 37, which recovers the original output signals, g4, g14 as can be seen in FIG. 6e.

Figure 7:
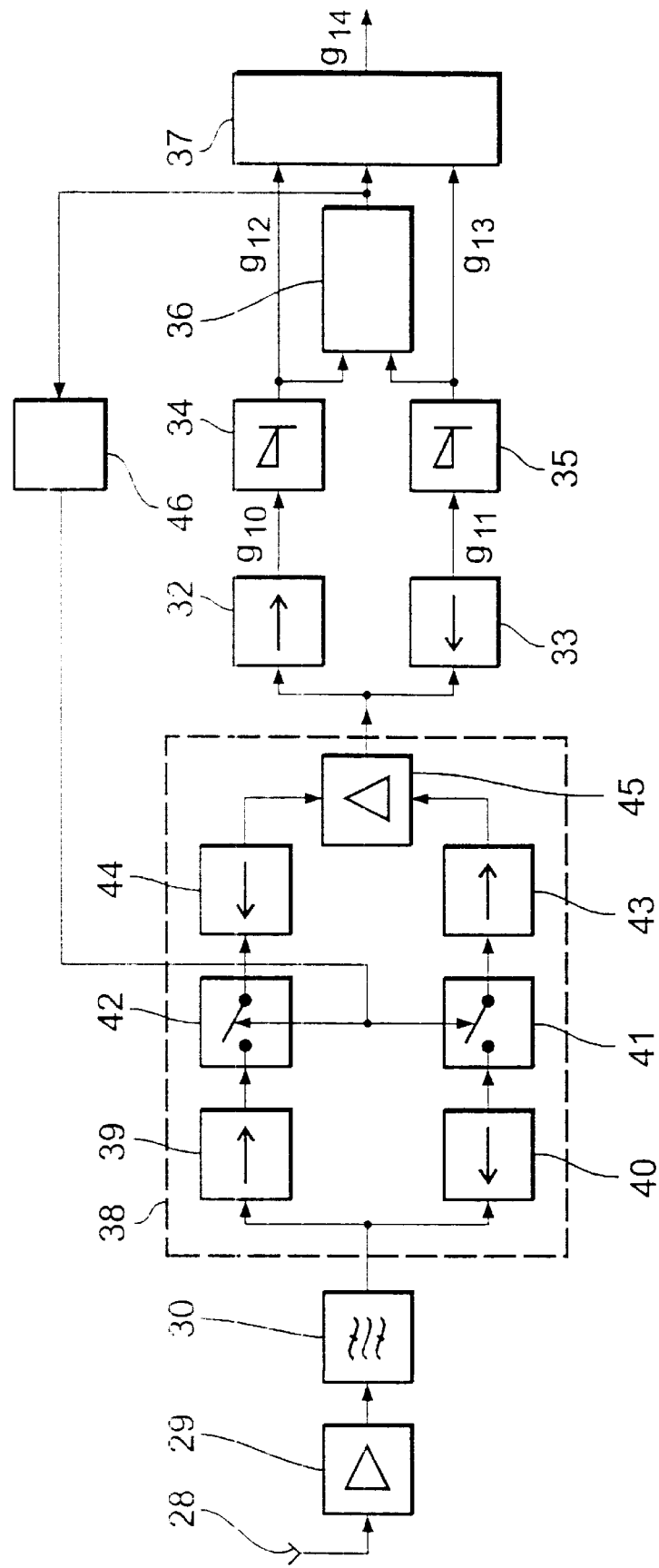
FIGS. 7 and 8 each show a modified form of the receiver illustrated in FIG. 4b with a noise suppression circuit.

FIG. 7 shows a modified form of the receiver shown in FIG. 4b, with a noise suppression circuit 38, which can be combined with other receivers for such Chirp signals. Due to the very close similarity of this receiver with the one shown in FIG. 4b, functionally equivalent components are labelled by the same reference signs in the two figures.

As in the previously described receiver, the signal chirped on the transmitter side is received through an antenna 28 and at first fed to an input amplifier 29 and a band-pass filter 30, which is tuned to the carrier frequency and thus filters out noise signals lying outside the transmission band. Subsequently, the signal is carried to the noise suppression circuit 38 and split into two parallel branches, in each of which two dispersion filters 39, 44 or 40, 43, inverse with respect to each other, are connected in series. During an active transmission of a logic LOW level as well as of a logic HIGH level, one of the two dispersion filters, 39 or 40, arranged on the input side, is tuned in such a way that a time compressed signal arrives at the output of this dispersion filter, 39 or 40. At the output of the other dispersion filter, 39 or 40, arrives a pulse that is time expanded to twice its original length. The two analogue switches 41, 42 interrupt the signal flow in the two branches symmetrically around the centre of the compressed pulse, so that the time compressed pulse is suppressed and only the time expanded pulse in the other branch remains. Hereby the analogue switches 41, 42 are controlled through the synchronizing circuit 46, that is triggered by the timing generator 36, and thus reproduces the timing of the output signal, and thus the transmission timing. The following dispersion filters 43, 44 generate the original pulse, with original width and correspondingly also with original amplitude, from the time expanded pulse. These pulses are then fed to the subtracter 45, at the output of which appears essentially the original pulse.

The matter is different for the noise that is caused by the noisy transmission path, and is received by the receiver together with the useful signal. This noise is at first shifted into different directions by the dispersion filters 39, 40. But the dispersion filter 43, 44, connected after, reverse this shift, so that the input noise is reconstructed in the two branches, except the very short portion cut out by the analogue switches 41, 42. Thus the subtraction by the subtracter 45 leads to extensive suppression of the noise picked up on the receiver side.

The further processing of the signal that was prepared in this manner then occurs as described in the description to FIG. 4b, starting after bifurcation 31.

Figure 8:
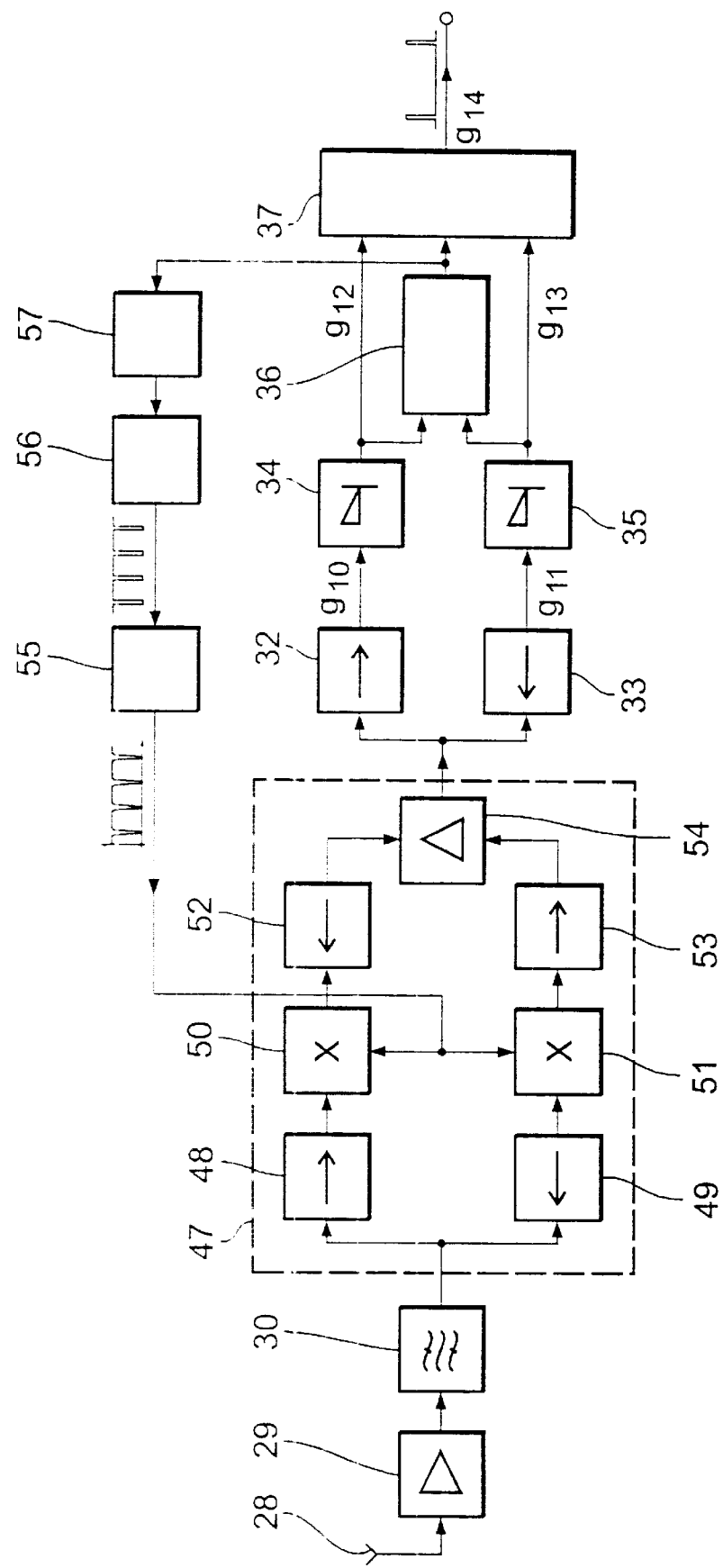

The receiver shown in FIG. 8 differs from the one described above and illustrated in FIG. 7 essentially by the design and the controlling of the noise suppression circuit 47. Due to the extensive similarity of the two circuits, functionally equivalent components or component modules are labeled by identical reference signs in FIGS. 7 and 8.

As with the receiver shown in FIG. 7, the chirped pulses are received by the antenna 28 and at first fed to an input amplifier 29 and a band-pass filter 30, which is tuned to the carrier frequency and thus filters out noise signals lying outside the transmission band.

Subsequently the signal is carried to the noise suppression circuit 47, which splits the signal into two parallel branches, that each contain two dispersion filters 48, 52 and 49, 53, inverse with respect to each other, connected in series. At the output of the noise suppression circuit 47 the two branches are joined by the subtracter 54, whereby the noise in the received signal is completely suppressed by the subtraction.

In contrast, the chirped signal is not cancelled by the subtraction in the subtracter 54, so that the signal/noise ratio is significantly increased. Hereby the dispersion filters 48, 49 on the input side are matched to the chirped signals, generated on the transmitter side, in such a way that a time compressed pulse with correspondingly increased amplitude appears at the output of one of the dispersion filters 48, 49, whereas a time expanded pulse with correspondingly reduced amplitude appears at the output of the other dispersion filter 49, 48. Upon arrival of the compressed pulses, the signal flow in the two branches is suppressed synchronously by the multipliers 50, 51,—as will be described in detail—so that the compressed pulse is cut out approximately along its envelope. The original pulse is then generated from the time expanded pulse by the dispersion filters 52, 53 connected after, so that essentially the originally received signal, with a significantly improved signal to noise ratio, arrives at the output of the subtracter 54.

The triggering of the multipliers 50, 51 occurs in fixed synchronization with the transmission timing rate, so that the signal in the two branches of the noise suppression circuit 47 can be suppressed exactly at the arrival of the time compressed pulse. For this, the receiver contains a synchronizing circuit 57, which on the input side is connected to the timing generator 36 for synchronization. Subsequently, Sinc-pulses with amplitude 1, lying inverted with the peak towards to zero, are generated by a pulse shaper 56 and a low-pass filter 55, and are then fed to the multipliers 50, 51. The multipliers 50, 51 multiply the signals in the two branches of the noise suppression circuit 47, either by zero or by unity, which accordingly either suppresses the signal or leaves the signal to pass essentially unchanged. Thus the multipliers 50, 51 here have the same effect as the switching elements 41, 42 in the variation of the noise suppression circuit 38 described before.

The scope of the invention is not limited to the previously listed preferred embodiments. A multitude of variations is possible that make use of the presented solution even in fundamentally different implementations. The embodiment examples shown here should only be seen as basic types of a wide spectrum of solutions.

What is claimed is:

1. A method for wireless communication with a medical device implanted in the human body, wherein in a transmitter an information input signal undergoes an angle modulation and reaches a receiver through a transmission channel, and further wherein angle modulated pulses carrying information possessing a frequency spectrum are generated in the transmitter and may be time compressed in the receiver using a frequency dependent delay time dispersion filter, and further wherein the pulses are created of shorter duration and increased amplitude compared to emitted pulses, wherein the pulses on a transmitter side undergo modulation or an encoding process and are imprinted with at least a part of information that constitutes a message, and wherein at least a part of the information that constitutes the message is also imprinted onto the angle modulation, wherein a quasi-Dirac pulse sequence is approximated in the transmitter and fed to a low-pass filter, the low pass filter characteristic of which possess a peak shortly before the critical frequency, and thus transforms the pulse sequence into a series of Sinc-pulses, having a shape of a Sinc function, which subsequently is carried to an amplitude modulator, which imprints a Sinc-shaped envelope onto each pulse of a carrier oscillation, and a signal generated after transformation is fed to a dispersive filter, at an output of which arrives a frequency modulated pulse sequence.

2. The method of claim 1, wherein the pulses are filtered according to a default filter response, and wherein the angle modulation on the transmitter side and the frequency dependent differential delay time response of the dispersion filter on a receiver side are matched, wherein spectral signal components of angle modulated pulses of an output signal arrive at an output of the dispersion filter essentially coincident, and with a corresponding increase in amplitude, due to a frequency dependent variable signal delay time of the dispersion filter.

3. The method of claim 2, wherein the angle modulated pulses are fed to at least two dispersion filters in the receiver, and further wherein variable delay time responses of the dispersion filters and modulation characteristics that are used on the transmitter side are matched in pairs, wherein spectral signal components of frequency modulated pulses arrive essentially coincident, with a corresponding increase in amplitude, at an output of only one of the at least two dispersion filters, while this compression does not take place for the corresponding other of the at least two dispersion filters.

4. The method of claim 1, wherein the pulses undergo additional modulation, the additional modulation selected from the group consisting of pulse position modulation, pulse code modulation, differential pulse code modulation, pulse delta modulation, and combinations thereof.

5. The method of claim 4, wherein the angle modulation and the additional modulation form independent, orthogonal, or approximately orthogonal modulation types.

6. The method of claim 1, wherein each pulse of a carrier frequency of an input signal is subjected to the angle modulation in the transmitter.

7. The method of claim 1, wherein an amplitude of pulses compressed by the dispersion filter is interpreted using a detector.

8. The method of claim 1, the angle modulation occurs according to a default modulation characteristic, that determines a time variation of a phase angle during a duration of a pulse, according to a predetermined time-variant behavior, an amplitude of an angle modulated pulse for imprinting information contained in an input signal is preset depending on the input signal, in the receiver the angle modulated pulses are fed to a dispersion filter, a delay time response of which is matched to the modulation characteristic of the angle modulation by a reverse time-variant behavior wherein spectral signal components of the angle modulated pulses arrive essentially coincident, and with a corresponding increase in amplitude, at an output of the dispersion filter, an amplitude of the pulses, compressed by the dispersion filter, is evaluated, for recovery of information contained in the input signal, using a detector, the detector being an amplitude demodulator.

9. The method of claim 8, wherein during pulse duration of pulse modulated signals, an angle, a frequency or a phase of a carrier frequency changes over time during the pulse duration, linearly or nonlinearly according to a predetermined profile, monotonically from a lower frequency or phase position to an upper frequency or phase position, or monotonically from an upper frequency of phase position to a lower frequency or phase position, wherein dispersion filters in the receiver possess a corresponding complementary response.

10. The method of claim 9, wherein the predetermined profile changes within a pulse sequence in relation of individual pulses to each other, and wherein the profile change is also part of information contained in the input signal.

11. The method of claim 1, wherein to facilitate communication between the transmitter and receiver, a predetermined digital reference signal is transmitted as an input signal to align the transmitter and the receiver, during communication facilitation an amplitude or a pulse duration of an output signal of the dispersion filter on a receiver side is measured, and a modulation characteristic used on a transmitter side, or a frequency dependent delay time response of the dispersion filter on the receiver side, is modified, until the pulse duration at an output of the dispersion filters in the receiver reaches a minimum value, or an amplitude reaches a maximum value.

12. The method of claim 1, wherein the signal flow in the receiver is split into two parallel branches, each with two dispersion filters with frequency dependent delay time characteristics, that are inverse with respect to each other, the signal flow in the two branches is connected through or interrupted for a predetermined time interval during each pulse, whereby the interruption or connection occurs synchronous to the transmission timing rate, the two branches are joined on the output side by a subtracter.

13. The method of claim 1, wherein the frequency of the carrier signal is in the range between 400 MHz and 1 GHz.

* * * * *